(12) United States Patent
Hill et al.

(10) Patent No.: US 6,182,665 B1
(45) Date of Patent: Feb. 6, 2001

(54) MATERNAL IMMUNE RESPONSIVENESS AS A PREDICTOR OF PREGNANCY OUTCOME

(75) Inventors: Joseph A. Hill, Brookline; Bonnie L. Bermas, Newton, both of MA (US)

(73) Assignee: Brigham and Women's Hospital, Boston, MA (US)

( * ) Notice: Under 35 U.S.C. 154(b), the term of this patent shall be extended for 0 days.

(21) Appl. No.: 09/087,723

(22) Filed: May 29, 1998

Related U.S. Application Data

(60) Provisional application No. 60/048,435, filed on Jun. 2, 1997, now abandoned.

(51) Int. Cl.$^7$ .................................................. A61B 19/00
(52) U.S. Cl. ......................... 128/898; 436/504; 436/518; 435/5; 435/7.9
(58) Field of Search ............................ 128/898; 436/504, 436/510, 518; 422/61; 435/7.9, 5; 600/300

(56) References Cited

U.S. PATENT DOCUMENTS

| | | | | |
|---|---|---|---|---|
| 4,016,250 | * | 4/1977 | Saxena | 436/504 |
| 4,094,963 | * | 6/1978 | Saxena | 422/61 |
| 5,223,440 | * | 6/1993 | Teng et al. | 436/510 |
| 5,281,522 | * | 1/1994 | Senyei et al. | 435/7.9 |
| 5,786,220 | * | 7/1998 | Pronovost et al. | 436/518 |

OTHER PUBLICATIONS

Bermas, et al., "T Helper Cell Dysfunction in Systemic Lupus Erythematosus (SLE): Relation to Disease Activity," *J. Clin. Immunol.* 14:169–177 (1994).

Brunham, et al., "Depression of the Lymphocyte Transformation Response to Microbial Antigens and to Phytohemagglutinin During Pregnancy," *J. Clin. Invest.* 72:1629–1638 (1983).

Cecere, et al., "The Interaction of Pregnancy and the Rheumatic Diseases," *Clinics in Rheum. Dis.* 7:747–768 (1981).

Cowchock, et al., "Fertility Among Women with Recurrent Spontaneous Abortions–The Effect of Paternal Cell Immunization Treatment," *Amer. J. Repro. Immunol.* 33:176–181 (1995).

Muchmore, et al., "In Vitro Evidence that Carbohydrate Moieties Derived from Uromodulin, an 85,000 Dalton Immuno–suppressive Glycoprotein Isolated from Human Pregnancy Urine, are Immunosuppressive in the Absence of Intact Protein," *J. Immunol.* 138:2547–2553 (1987).

Muluk, et al., "Correlation of In Vitro CD4$^+$ T Helper Cell Function with Clinical Graft Status in Immunosuppressed Kidney Transplant Recipients," *Transplantation* 52:284–291 (1991).

Nelson, "Maternal–Fetal Immunology and Autoimmune Disease," *Arthr. & Rheum.* 39:191–194 (1996).

Schulick, et al., "Value of In Vitro CD4$^+$ T Helper Cell Function Test for Predicting Long–Term Loss of Human Renal Allografts," *Transplantation* 57:480–482 (1994).

Stallmach, et al., "Cytokine Production and Visualized Effects in the Feto–Maternal Unit: Quantitative and Topographic Data on Cytokines During Intrauterine Disease," *Lab. Invest.* 73:384–392 (1995).

Stirrat, "Recurrent Miscarriage II: Clinical Associations, Causes and Management," *The Lancet* 336:728–733 (1990).

Tafuri, et al., "T Cell Awareness of Paternal Alloantigens During Pregnancy," *Science* 270:630–633 (1995).

Tartoff, et al., "NK Cell Activity and Skin Test Antigen Stimulation of NK like CMC In Vitro Are Decreased to Different Degrees in Pregnancy and Sarcoidosis," *Clin. Exp. Immunol.* 57:502–510 (1984).

* cited by examiner

*Primary Examiner*—David J. Isabella
*Assistant Examiner*—Kelly O'Hara
(74) *Attorney, Agent, or Firm*—Michael A. Sanzo; Pillsbury Madison & Sutro LLP

(57) ABSTRACT

A method for predicting whether a pregnant woman will be able to carry a fetus to viability by determining her immunological responsiveness to recall antigens. Women, particularly women with a history of recurrent spontaneous abortion, who have a responsiveness that is no higher than the responsiveness of women known to have had a successful pregnancy, have a high probability of maintaining gestation until viability.

15 Claims, 2 Drawing Sheets

MATERNAL IMMUNE RESPONSIVENESS AS A PREDICTOR OF PREGNANCY OUTCOME

CROSS REFERENCE TO RELATED APPLICATIONS

This present application claims the benefit of U.S. provisional application No. 60/048,435, filed on Jun. 2, 1997 (now abandoned).

STATEMENT OF GOVERNMENT SUPPORT

The work leading to this invention was supported by one or more grants from the U.S. Government. The U.S. Government therefore has certain rights in the invention.

FIELD OF THE INVENTION

The present invention is directed to a method for determining whether a pregnant woman will successfully complete gestation based upon her immunological responsiveness to recall antigens.

BACKGROUND OF THE INVENTION

Recurrent spontaneous abortion, defined as three or more unexplained pregnancy losses prior to 20 weeks of gestation, occurs in approximately 0.3% of couples who desire children (Stirrat, *Lancet* 336:728–733 (1990)). Among the factors identified as causing this disorder are: genetic or chromosomal abnormalities (3–5% of cases); endocrine etiologies (17%); infections (5%); and mularian anomalies (10%). The etiology of the remaining 50–60% of miscarriages is uncertain, but there are reasons to suspect that immunological factors may play a role.

Pregnancy is accompanied by a decline in the reactivity of maternal T-cells to HLA antigens (Tafuri, et al., *Science* 270:630–633 (1995)) and by a diminished immunological responsiveness of the mother (see e.g., Brunham et al., *J. Clin. Invest.* 72:1629–1638 (1983); Muchmore et al., *J. Immunol.* 138:2547–2553 (1987); and Tartof, *Clin. Exp. Immunol.* 57:502–510 (1984)). This suggests that maternal immunological changes may help provide an environment conducive to fetal development.

Additional evidence comes from observations made in patients with immunological disorders. Women with rheumatoid arthritis (RA), generally experience an improvement in their symptoms during pregnancy (Cecere, et al., *Clin. Rheum. Dis.* 7:747–768 (1981) This may be related to the down-regulation of tumor necrosis factor alpha, a cytokine suspected of contributing to the severity of RA (Stalimach, et al., *Lab. Invest.* 73:384–392 (1995)). In contrast, women with systemic lupus erythematosus (SLE) often experience a worsening of the disease when they become pregnant (Nelson, *Arthritis Rheum.* 139:191–194 (1996)). Diminished interleukin-2 production in response to recall antigens correlates with SLE disease activity and disease flares (Bermas, et al., *J. Clin. Immunol.* 14:169–177 (1994)). Since a similar decrease is also seen during normal pregnancy, this may explain why pregnant women with SLE experience an exacerbation of their symptoms.

Although immunological changes have been associated with pregnancy, the extent to which these changes are necessary for a successful completion of gestation has not been established. A test which correlates pregnancy outcome with a readily measurable immunological parameter would represent a clear advance in reproductive biology and would be of benefit in clinical practice. Ideally, such a test would be simple to perform and effective for the majority of pregnant women.

SUMMARY OF THE INVENTION

The present invention is based upon the discovery that the immunological responsiveness of a pregnant woman to recall antigens can be used to predict whether she will carry a fetus to the point of viability. Women that fail to undergo a normal suppression of immunoresponsiveness have an increased risk of having a spontaneous abortion. In contrast, even women with a history of recurrent spontaneous abortion will maintain gestation to fetal viability when their responsiveness to recall antigens is reduced to an extent comparable to that of normal women.

In its broadest aspect, the invention is directed to a method for predicting if a pregnant woman will carry a fetus to viability by assaying her immunological responsiveness to recall antigens and comparing the results to those of a control group made up of one or more pregnant women known to have carried a fetus to viability. In cases where the woman undergoing testing shows a responsiveness that is not significantly greater than the responsiveness of the control group, it may be predicted that she will carry the fetus to viability. As used herein, a fetus has reached the point of viability when it is capable of surviving outside of its mother's womb, either with or without medical intervention. A woman has a significantly different responsiveness than the control group when $p<0.05$ using Student's T test.

Preferred recall antigens are those that nearly all of the population has been exposed to and include influenza antigens, tetanus antigens and Candida antigens. In general, assays should be performed on women between 6 and 9 weeks of gestation and will be most beneficial for women that have a history of reproductive failure, e.g., a history of having had at least one spontaneous abortion.

A preferred method for determining the immunological responsiveness of women is by collecting peripheral blood leukocytes (PBLs) and measuring their proliferation both in the presence and absence of the antigen. Cultures not exposed to the antigen serve as a measure of background proliferation, i.e., proliferation not induced by antigen. Background proliferation is subtracted from proliferation in the presence of antigen to determine immunological responsiveness. A preferred method for determining the rate at which cells proliferate is by determining their uptake up tritiated thymidine.

An alternative method for measuring responsiveness to a recall antigen is to determine the degree to which the antigen induces the secretion of a cytokine or growth factor related to the immune response. The preferred cytokines and growth factors for measurements are any of the interleukins, tumor necrosis factors, interferons, colony stimulating factors, leukemia inhibitory factor, transforming growth factors, or epidermal growth factor.

The ability to evaluate the likelihood that a woman will carry a fetus to viability can be used as part of a therapeutic program designed to reduce the likelihood that a pregnant woman will have a spontaneous abortion. This can be accomplished by first evaluating the likely outcome of pregnancy by one of the methods discussed above. If the results do not indicate that it is probable that the woman being tested will carry the fetus to viability, then she may be administered an immunosuppressive agent in an amount and for a duration sufficient to decrease her responsiveness to recall antigens. Ideally, the reduction in responsiveness should be just sufficient so that it no longer differs from the control group to a statistically significant degree. The effectiveness of the treatment regimen can be monitored by periodically repeating assays of responsiveness to recall antigens.

In a somewhat more specific aspect, the present invention is directed to a method for predicting if a pregnant woman will carry a fetus to viability by: a) obtaining PBLs from the woman undergoing testing; b) measuring the proliferation of the PBLs in the presence of one or more recall antigens; c) measuring the proliferation of the PBLs in the absence of the recall antigens; d) determining a stimulation index for the woman by dividing the amount of proliferation in the presence of recall antigens by the amount in the absence of the antigens; and e) predicting that the woman will carry the fetus to viability if the stimulation index is less than three.

The preferred method for assaying the proliferation of PBLs is by measuring the extent to which they incorporate tritiated thymidine and the preferred antigens are those associated with influenza A, tetanus and Candida. Typically, the method should be performed on a woman between 6 and 9 weeks of gestation and it is expected that it will find its greatest use for women selected because of a history of reproductive failure, e.g., a history of having had at least one spontaneous abortion. As with the method described above, the present method can be used as part of a therapeutic regimen for reducing the likelihood that a pregnant woman will experience a spontaneous abortion. This can be accomplished by evaluating the likelihood of her carrying a fetus to viability using the present method and then, if this evaluation indicates that it is not probable that she will carry the fetus to viability, administering an immunosuppressive agent. The agent should be administered in an amount and for a duration sufficient to decrease her stimulation index to less than three.

DETAILED DESCRIPTION OF THE INVENTION

Figure 1:
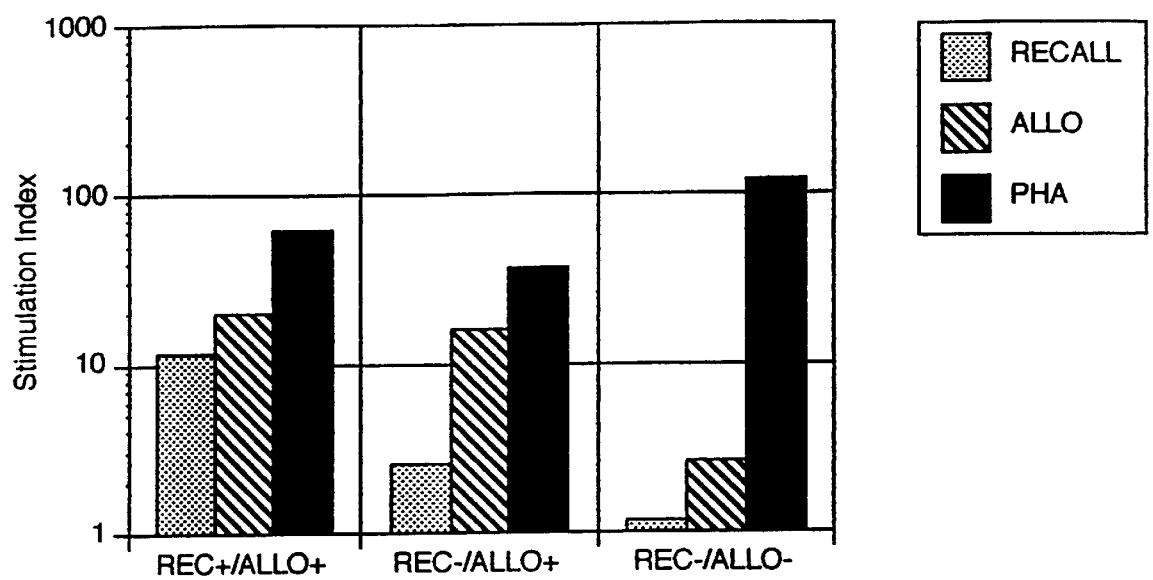
FIG. 1: Observed Proliferation Patterns in PBLs from Pregnant Women: Experiments were performed in which peripheral blood mononuclear cells (PBMC) were isolated from pregnant women and their responsiveness to recall antigens, alloantigens and phytohemagglutinin was determined. The three types of patterns that were obtained are shown in the figure. The left side of the panel shows positive (stimulation index >3) proliferative responses to recall antigens (REC), alloantigens (ALLO), and phytohemagglutinin (PHA). The responsiveness to influenza and tetanus antigens was measured and the maximum response to either stimulus is plotted. The middle of the panel shows loss of response to recall antigens but maintenance of response to alloantigens and phytohemagglutinin. The right side of the figure shows a loss of responsiveness to both recall antigens and alloantigens.

The present invention is based upon the concept that the loss of recall antigen responsiveness in pregnant women can be associated with the maintenance of the fetus. This concept is supported by experiments showing that only 40% of pregnant women with a history of recurrent spontaneous abortion (RSA) experience a loss of responsiveness to recall antigens comparable to the loss observed in pregnant fertile women (see Examples section). Importantly, all of the 40% of RSA women evidencing comparable immunosuppression had a successful pregnancy, whereas two-thirds of the RSA women that did not evidence comparable immunosuppression subsequently had a spontaneous abortion. Thus, assays of the responsiveness of pregnant women to recall antigens can be used as an effective means for predicting whether the fetus will be carried to term or is at risk for being spontaneously aborted. By choosing recall antigens that are widely distributed among the population, and using standard tests of immuno-responsiveness, a procedure that can be widely used in the clinical practice of obstetrics and gynecology has been developed.

A. Method for Predicting if a Woman Will Carry a Fetus to Viability

The present method for determining whether a pregnant woman will maintain gestation until the fetus is viable involves assaying the immunological responsiveness of the woman to one or more recall antigens. Although, any type of recall antigen can be used in the assay, the most preferred are those to which the vast majority of the population has been exposed. For example, antigens associated with childhood vaccination are widely available from commercial sources and should provoke a strong response in nearly all healthy individuals that are not immunosuppressed. Thus, antigens associated with diphtheria, pertussis, tetanus, measles, mumps and rubella would all be suitable choices for assay. Alteratively, antigens associated with diseases that nearly all people have been exposed to, e.g., influenza A or Candida, could be prepared using standard, well-established methods and used in assays. For example, influenza A virus may be prepared by infecting chicken eggs with a stock of virus, harvesting the allantoic fluid, and then aliquoting and freezing virus at −70° C. (see Shearer, et al., *J. Immunol.* 137:2514–2521 (1986)).

Not all antigens will be effective for every patient. An assay should involve the use of an antigen to which a woman has been previously exposed and should not involve antigens that may produce anomalous results due to active or recent infection. For example, the antigens associated with childhood vaccines would be a poor choice in cases where the woman being tested had not been vaccinated. Similarly, the influenza A antigen would be a poor choice if the woman had recently experienced an influenza infection. For this reason, it is advisable to have more than one antigen available for use in assays. Not only will this help to ensure that an effective assay is available for most women, it will also provide a means for confirming assay results with a follow-up procedure.

Any type of assay for measuring immunological responsiveness to recall antigens may be used. However, in all cases, it will be helpful to compare, directly or indirectly, the responsiveness of a given woman with the responsiveness of a control group made up of pregnant women known to have carried a fetus to viability. Typically, responsiveness will be measured using peripheral blood leukocytes, e.g., peripheral blood mononuclear cells, and measurements will be made both in the presence and absence of recall antigen. Assays performed in the absence of the antigen serve as "background" measurements of non-induced proliferation. These measurements would be subtracted from the proliferation seen in the presence of antigen to determine responsiveness. The responsiveness of cells from the control group, could, in principle, be measured at the same time as measurements were made on the woman undergoing testing. However, it will generally be more convenient to have established a range for the control group that can be repeatedly used in future testing. It is advisable that at least one sample known to be taken from a woman who has carried a fetus to viability be included in test assays to ensure that it gives the expected results and that the assay is therefore working properly.

The determination of whether it is probable that a given pregnant woman will carry a fetus to viability is based upon a comparison between the results obtained for the woman and the results of the control group. Results indicating that a woman has a responsiveness to the tested recall antigen which is not significantly greater than the responsiveness of the control group indicates that the woman should carry the fetus to viability. Results showing a significantly greater immunological responsiveness indicates that the woman tested is at risk for having a spontaneous abortion. In all cases, the significance of the differences observed in assays can be determined using Student's t test, with a p value of less than 0.05 indicating clear significance. If desired, alternative forms of statistical analysis may be used.

An alternative method for analyzing assay results is to use a simple parameter for distinguishing significant and non-significant results. For example, in the peripheral blood leukocyte proliferation assay discussed below, it has been found that women giving a stimulation index of less than 3 successfully carry a fetus to viability, whereas women with a higher stimulation index have an increased risk for having a spontaneous abortion. Similar types of simple criteria for evaluating test results may be established for other assays as well.

Pregnant women should be tested early in pregnancy, with 6 to 9 weeks gestation being preferred. Although the test may be used for testing pregnant women in general, it is expected that its greatest utility will be in the testing of women with a history of reproductive failure, e.g., a history of recurrent spontaneous abortion, unexplained infertility or implantation failure following in vitro fertilization and embryo transfer.

Any assay which can effectively measure immune responsiveness to recall antigens is compatible with the present invention. However, two types of assays are preferred, both involving the use of peripheral blood leukocytes. The first type of preferred assay measures cell proliferation and may include a determination of increases in cell number, cell growth, cell division or cell expansion. Typically, these are measured by determining cell number, cell weight, or by the cellular incorporation of radiolabeled nucleosides, amino acids, or other precursor molecules. In the most preferred version of this type of assay, the proliferation of cultured peripheral blood polymorphonuclear cells is determined by pulse-labeling cultures with tritiated thymidine, a nucleoside precursor that is incorporated into newly synthesized DNA. Thymidine incorporation provides a quantitative measure of the rate of DNA synthesis which is directly proportional to the rate of cell division. Incorporation of labeled nucleoside can be determined by scintillation counting in a liquid scintillation spectrophotometer. Scintillation counting typically produces data in counts-per-minute (cpm) which may be used as a standard measure of immune cell responsiveness. The cpm obtained for cultures not exposed to recall antigen may be divided into the cpm obtained from recall antigen-stimulated cells to give a stimulation index.

A second preferred method for determining immunological responsiveness involves assays measuring cytokine or growth factor production. Among the factors that can be measured using well established assays are: any of the interleukins, tumor necrosis factors, interferons, colony stimulating factors, leukemia inhibitory factor, transforming growth factors, or epidermal growth factor. Again, the preferred cells for use are peripheral blood polymorphonuclear cells collected from pregnant women and cultured. The concentration of cytokines and growth factors may be determined using radioimmunoassays, enzyme-linked immunosorbent assays, bioassays, or measurements of mRNA levels. Immunoassays are well-known in the art and can include both competitive assays and immunometric assays (see generally Ausubel, et al., *Current Protocols in Molecular Biology,* 11.2.1–11.2.19 (1993); Laboratory Techniques in Biochemistry and Molecular Biology, Work et al., ed. (1978)).

There are a number variations that have been introduced into both proliferation and cytokine assays, any of which may be incorporated as part of the present invention. The only essential requirement is that the assay remain capable of determining the immunological responsiveness of a woman to a given recall antigen. In a particularly preferred assay, polymorphonuclear leukocytes are isolated from the whole blood of pregnant women by centrifugation, washed and then suspended in medium with antibiotic, e.g., RPMI medium (Gibco, Grand Island, N.Y.) with penicillin/streptomycin and 1% glutamine. An equivalent number of viable cells (e.g., $2 \times 10^5$) are cultured on plates (e.g., 96 well flat bottom plates) either in medium alone or in medium containing recall antigen. Human serum may also be added to samples, typically to a final concentration of about 5%.

The cultures are incubated for a fixed period of time (e.g., for seven days at 37° C. and 5% $CO_2$) and then tritiated thymidine is added to the culture medium. After incubation for an additional period of time, e.g., 18 hours, cells are harvested, washed and counted to determine the extent to which radioactivity has been incorporated. A stimulation index for each sample is then determined by dividing the amount of proliferation, as determined by radioactivity incorporation, seen in the presence of recall antigen by the amount of proliferation observed in the absence of recall antigen. Samples that have a stimulation index of less than 3 indicate that the woman from which they were derived should carry a fetus to viability. Samples that have a stimulation index of greater than 3 suggest that the woman from which they were derived has a substantial risk of having a spontaneous abortion.

C. Therapeutic Regimens Based Upon Predictions of Pregnancy Outcome

The methods discussed above can be used as part of a therapeutic regimen for reducing the likelihood of spontaneous abortion. If the immunological responsiveness of a woman is such that the methods indicate that it is not probable that she will carry a fetus to viability, the woman may be administered an immunosuppressive agent to reduce the likelihood of miscarriage. Immunosuppressive agents that may be administered include: cyclosporine (Sandimmune®, Sandoz); anti-thymocyte immunoglobulin (Atgam®, Upjohn); tacrolimus (Prograf®, Fujisawa); antibody to CD3 (Orthoclone®, Ortho); intravenous immunoglobulin; progesterone; and azathioprine (Imuran®, Burroughs Wellcome). The exact dosage and route of administration will depend upon the particular immunosuppressive selected, but any dosage form and route of administration is compatible with the method.

In general, the amount of immunosuppressive given should be just adequate to lower the immune responsiveness of the woman being treated to a point where the methods discussed above indicate that she will carry the fetus to viability. It may be desirable to start with a low initial dose of immunosuppressive in order to ensure that the patient is able to tolerate the medication without unacceptable side effects. Once this is established, the dosage may be adjusted upward until assays reveal that the patient's responsiveness to recall antigens indicates that gestation will be maintained to fetal viability. Immunosuppression will need to be maintained throughout the entire pregnancy and therefore periodic testing of immune responsiveness will need to be performed. Adjustments in dosage can be made according to the results obtained using procedures that are well established and routine in clinical medicine.

D. Utility of Methods

The present invention provides a means for advising pregnant women, particularly women who have a history of reproductive failure, whether their pregnancy is likely to proceed to fetal viability or they are at increased risk for having a spontaneous abortion. As can be seen from the results discussed in the example below, the method is very reliable in identifying women that will proceed to fetal viability. The results also suggest that the majority of women that maintain a high immunological responsiveness to recall antigens will have a spontaneous abortion and these women may therefore want to undergo therapies designed to improve their chances of maintaining their pregnancy. The most obvious approach to treating such women is to administer drugs that reduce their responsiveness to recall antigens to that more typical of women that carry fetuses to viability. A particular advantage of the method is that it utilizes assay procedures that have long been known in the art and relies upon antigens that are commonly available and which can produce meaningful results for the vast majority of women.

EXAMPLES

The present example assesses T helper cell function of pregnant and non-pregnant women using an in vitro assay which measures proliferative responses to recall antigens. It was found that the majority of women with a history of recurrent spontaneous abortions when pregnant failed to diminish their responsiveness to recall antigens in contradistinction to fertile pregnant women. This lack of modulation of T helper cell activity was significantly associated with a poor pregnancy outcome in women with a history of recurrent pregnancy loss. This approach is useful for predicting pregnancy outcome in women and in designing and implementing therapies to treat recurrent spontaneous abortion.

A. Materials and Methods

Study Subjects:

Study subjects included 28 non-pregnant (within 4–12 months of a recent pregnancy loss) and 20 pregnant women (6–9 weeks gestation with a documented fetal heart on ultrasound) who were being seen in the Recurrent Miscarriage Clinic within the Center for Reproductive Medicine at Brigham Women's Hospital between January 1995 and June 1996. The women were between 22 and 42 years of age and had a history of at least three (range, 328) prior first-trimester spontaneous abortions of unexplained etiology, with or without a prior ectopic gestation or live birth. Five of the pregnant patients with a history of recurrent spontaneous abortion (RSA) also had unexplained subfertility and had conceived following in vitro fertilization and embryo transfer. Individuals with chromosomal, anatomic endocrine and endometrial defects, infectious diseases and antiphospholipid antibodies as potential etiologies of their pregnancy losses were not included in this study. Pregnant fertile controls (n=15), between 6 and 9 weeks of gestation, who had at least one healthy pregnancy and no history of prior pregnancy losses were recruited from the Center for Family Planning of the Brigham & Women's Hospital at the time they were having an elective termination of pregnancy. Paid volunteer, non-pregnant fertile controls (n=13), aged 20–45 who had at least one healthy pregnancy and no prior pregnancy losses, were recruited from the staff of the Brigham & Women's Hospital. All of the study participants were non-smokers, in excellent health with no history of atopy, allergies, or recent infection. In addition, none of the women were taking any medications other than multivitamins.

In Vitro Tests for T Helper Function

Whole blood samples from individuals were collected into vacutainer tubes containing sodium heparin (Becton Dickinson, Franklin Lakes, N.J.) and were held overnight at room temperature. Peripheral blood mononuclear cells (PBMC) were isolated by Ficoll-hypaque (Pharmacia, Uppsala) centrifugation, washed twice and resuspended in RPMI (Gibco, Grand Island, M.Y.) with penicillin/streptomycin and 1% glutamine. Viable cells were determined by trypan blue exclusion and then diluted to a concentration of $2 \times 10^6$ cells/ml. $2 \times 10^5$ cells of PBMC were cultured in 96 well flat bottom plates (Falcon, Becton Dickinson, Franklin Lakes, N.J.) in medium alone or were stimulated in the presence of: a) influenza A, Bangkok RX73 at a final dilution of 1:500; b) tetanus from the Massachusetts Department of Health, Boston, Mass. at a final dilution of 40 IF/ml.; c) alloantigens (ALLO), PBMCs from volunteer donors, which were irradiated with 5,000 rads and resuspended at $1 \times 10^5$ cells/well; and d) phytohemagglutinin (PHA) at a final concentration of 1:100. Human AB+ serum was added to each well to a final concentration of 5%.

Plates were incubated for 7 days at 37° C. and 5% $CO_2$. On day 6, the cultures were pulsed with 1 vCi of $[^3H]$ thymidine (New England Nuclear, Boston, Mass.) and harvested 18 hours later. Stimulation index was calculated by dividing the counts per minute of the stimuli tested by the counts per minute of the background media response for each individual. A positive response was considered to be a stimulation index of 3 or greater.

Statistical Analysis of the Data

Data are represented as mean ±SEM. Student's t test was used to compare means, for two by two analysis, Chi-squared was used. $P < 0.05$ was considered statistically significant.

B. Results

Patterns of T Helper Responses in Patients With RSA and Controls

PBMCs from 48 women with a prior history of recurrent spontaneous abortion (28 non-pregnant and 20 pregnant) as well as 28 fertile controls (13 non-pregnant and 15 pregnant) were tested for their proliferative response to influenza virus, tetanus, alloantigens and phytohemagglutinin. Three patterns of responsiveness to the stimuli tested were identified and the results are presented in FIG. 1.

In the first pattern, cells proliferated both to recall antigens and to alloantigens, designated (+/+). In the second pattern, study subjects lost responsiveness to recall antigens but maintained responsiveness to alloantigens, designated (−/+). Subjects were designated (−/+) only if they lost responsiveness to both FLU and TET to circumvent the issue of variability in immunization and exposure history. If they responded to either of these stimuli, a positive recall response was assigned. In the third pattern, responsiveness to both recall and alloantigens was lost (−/−). PHA was used as a positive control.

Figure 2:
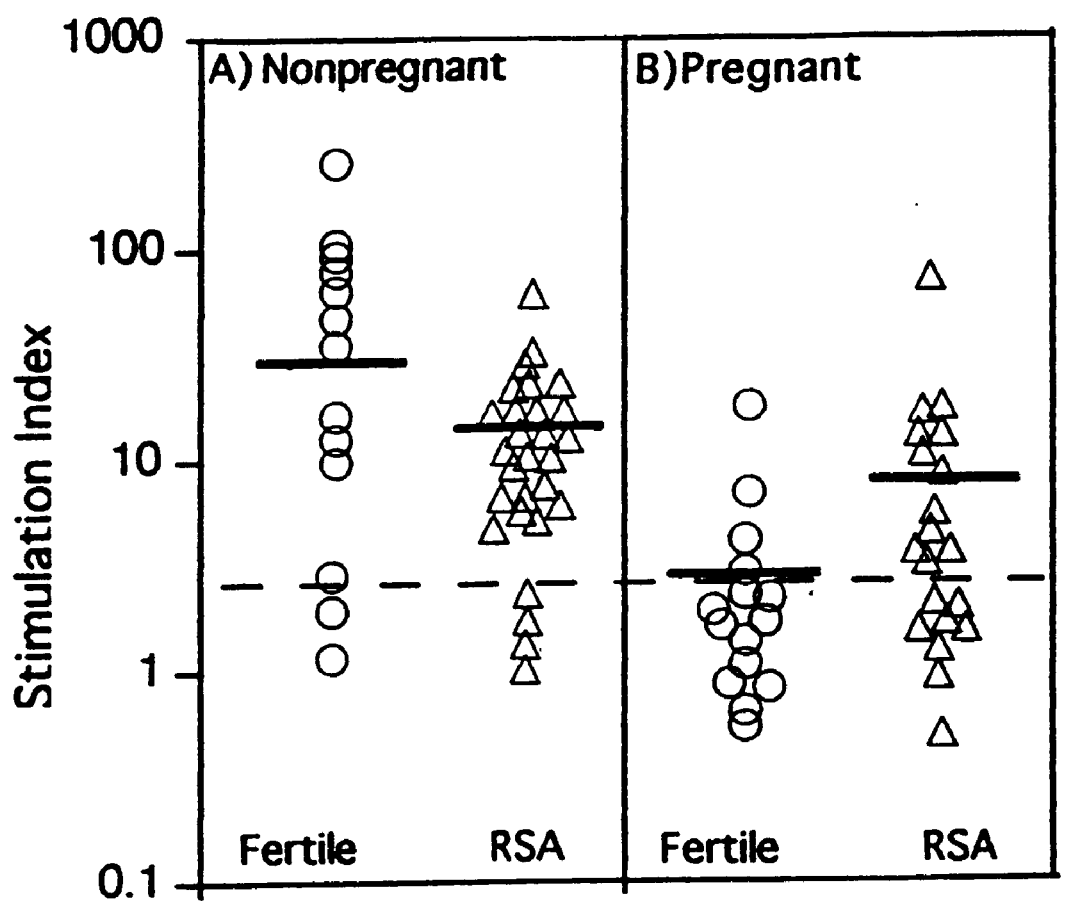
FIG. 2: Mean and Individual Values for Proliferative Responses of PBMCs: The figure shows the mean and individual values for proliferative responses to the recall antigens of influenza and tetanus. Panel A depicts results obtained for non-pregnant fertile control women (Fertile)○ and non-pregnant women with a history of recurrent spontaneous abortion (RSA)Δ. Panel B shows the results for pregnant fertile control women (Fertile)○ and pregnant women with a history of recurrent spontaneous abortion (RSA)Δ.

Non-pregnant fertile controls and non-pregnant women with recurrent spontaneous abortion showed a similar ability to respond to recall antigens (85% and 89%, respectively) (Table 1) During pregnancy, however, these responses diverged such that 73% of pregnant controls lost responsiveness to recall antigens during gestation (non-pregnant fertiles versus pregnant fertiles, p=0.007), while only 40% of pregnant women with a history of recurrent spontaneous abortion lost responsiveness to recall antigens (non-pregnant RSA versus pregnant, p=NS). A summary of the stimulation indices to recall antigens in all four groups is presented in FIG. 2. The mean stimulation index to recall antigens in women with a history of recurrent spontaneous abortion did not diminish during pregnancy (p=NS), whereas in pregnant fertile controls, the mean stimulation index to recall antigens was significantly lowered when compared to non-pregnant controls (p=0.005).

TABLE 1

Summary of Responsiveness to Recall Antigens According to Patient Group

| Study Group | Recall +/ Allo + | Recall −/ Allo + | Recall −/ Allo − |
|---|---|---|---|
| Nonpregnant Fertile (N = 13) | 11 (85%) | 2 (15%) | 0 (0%0 |
| Nonpregnant RSA (N = 28) | 25 (89%) | 2 (7%) | 1 (4%) |
| Pregnant Fertile (N = 15) | 4 (27%) | 8 (53%) | 3 (20%) |
| Pregnant RSA (N = 20) | 12 (60%) | 7 (35%) | 1 (5%) |

Relationship of Recall Antigen Responsiveness to Pregnancy Outcome in Patients with a History of Unexplained Recurrent Spontaneous Abortion All eight women with a history of recurrent spontaneous abortion who lost responsiveness to recall antigens while pregnant carried the pregnancy to delivery (Table 2). However, in those women with a history of RSA whose PBMCs proliferated in response to recall antigens while they were pregnant, only 33% carried that pregnancy to term. The relationship of recall antigen responsiveness to pregnancy outcome in women with a history of RSA was statistically significant at a level of p<0.02. When the analysis was done excluding the five patients undergoing in vitro fertilization, the significance remained at p<0.02. The overall pregnancy success rate (52%) in patients with recurrent spontaneous abortion was similar to that seen in other series (Cowchuck, et al., *Amer. J. Reprod. Immunol.* 33:176–181 (1995)).

TABLE 2

Pregnancy Outcome in Women With a History of Recurrent Spontaneous Abortion Aecording to T Cell Functional Status

|  | Recall Positive (N = 12) | Recall Negative (N = 8) |
|---|---|---|
| Recurrent Pregnancy Loss | 8 | 0 |
| Pregnancy Success | 4 | 8 |

C. Discussion

The experiments herein demonstrate that significantly fewer women with a history of spontaneous abortion are able to down-regulate responsiveness to recall antigens in the first trimester of pregnancy. Of those women who were able to do so, 100% carried the pregnancy to term. Of those who failed to down modulate recall responsiveness, 67% had recurrent loss of the pregnancy. This demonstrates that diminished proliferation of PBMCs in response to recall antigens is associated with a favorable pregnancy outcome and, conversely, that a lack of this immunosuppression portends poor pregnancy outcome in patients with prior recurrent spontaneous pregnancy losses.

Five women with a history of recurrent spontaneous miscarriage also had difficulty conceiving and had become pregnant following in vitro fertilization and embryo transfer. The inclusion of these individuals, however, did not alter the statistical outcome of the study. The data suggests that once implantation occurs following in vitro fertilization and embryo transfer, pregnancy maintenance is dependent upon immunomodulation just as in non-assisted reproduction. The data also indicates that diminished responsiveness to third-party alloantigens is not necessary for pregnancy maintenance, supporting the findings in the transplant literature (Mulluk, et al., *Transplantation* 52:284–291 (1991); Schulick, et al., *Transplantation* 57:480–482 (1994)).

Overall, the study demonstrates that fertile controls decreased their responsiveness to recall antigens when pregnant, while in women with a history of recurrent spontaneous abortion, this down regulation was more sporadic. Diminished responsiveness to recall antigens could be a marker for more global immunosuppression. Thus, in normal pregnancy, either due to the hormonal environment or to direct immune signaling at the maternal fetal interface, decreased responsiveness to recall antigens occurs in a manner similar to that in immunosuppressed transplant recipients. Immune modulation may lead to a decrease in the secretion of proinflammatory cytokines in a manner that is advantageous for pregnancy maintenance. Overall, the assessment of recall antigen responsiveness as described in this study, is useful in predicting pregnancy outcome and in the design of therapeutics for women with recurrent spontaneous abortion.

All references cited are fully incorporated by reference. Having now fully described the invention, it will be understood by those of skill in the art that the invention may be performed within a wide and equivalent range of conditions, parameters, and the like, without affecting the spirit or scope of the invention or any embodiment thereof.

What is claimed is:

1. A method for predicting if a pregnant woman will carry a fetus to the point of viability comprising:
   a) assaying the immunological responsiveness of said woman to one or more recall antigens;
   b) comparing the responsiveness of said woman as measured in step a) to the responsiveness of a control group made up of one or more pregnant women known to have carried a fetus to viability;
   c) predicting that said woman will carry said fetus to viability if the immunological responsiveness of said woman is not significantly greater than the immunological responsiveness of said control group.

2. The method of claim 1, wherein said recall antigens are selected from the group consisting of: influenza antigens; tetanus antigens; and Candida antigens.

3. The method of claim 1, wherein said woman is between 6 and 9 weeks of gestation.

4. The method of claim 1, wherein said woman is selected for said method because of a history of having had at least one spontaneous abortion.

5. The method of claim 1, wherein immunological responsiveness is determined by measuring the proliferation of peripheral blood leukocytes.

6. The method of claim 1, wherein immunological responsiveness is determined by measuring the secretion of a cytokine or growth factor.

7. The method of claim 6, wherein said cytokines are secreted by peripheral blood leukocytes.

8. The method of claim 7, wherein said cytokine or growth factor is selected from the group consisting of: interleukin 1–15; tumor necrosis factors; interferons; colony stimulating factors; leukemia inhibitory factor; transforming growth factors; or epidermal growth factor.

9. A method for reducing the likelihood that a pregnant woman will experience a spontaneous abortion, comprising:
   a) evaluating the likelihood that said woman will carry a fetus to viability by the method of claim 1; and
   b) if the results of step a) do not indicate that said woman will carry said fetus to viability, administering an immunosuppressive agent to said woman in an amount and for a duration sufficient to decrease her responsiveness to recall antigens.

10. A method for predicting if a pregnant woman will carry a fetus to the point of viability, comprising:
    a) obtaining peripheral blood leukocytes from said woman;
    b) measuring the proliferation of said peripheral blood leukocytes in the presence of one or more recall antigens;
    c) measuring the proliferation of said peripheral blood leukocytes in the absence of said one or more recall antigens;
    d) determining the stimulation index of said woman by dividing the amount of proliferation determined in step b) by the amount of proliferation determined in step c); and
    e) predicting that said woman will carry said fetus to viability if said stimulation index is less than three.

11. The method of claim 10, wherein proliferation is determined by measuring the incorporation of tritiated thymidine by cultured peripheral blood leukocytes.

12. The method of claim 10, wherein said recall antigens are selected from the group consisting of: influenza antigens; tetanus antigens; and Candida antigens.

13. The method of claim 10, wherein said woman is between 6 and 9 weeks of gestation.

14. The method of claim 10, wherein said woman is selected for said method because of a history of having had at least one spontaneous abortion.

15. A method for reducing the likelihood that a pregnant woman will experience a spontaneous abortion, comprising:
    a) evaluating the likelihood that said woman will carry a fetus to viability by the method of claim 10;
    b) if the evaluation of step a) does not indicate that said woman will carry said fetus to viability, administering an immunosuppressive agent to said woman in an amount and for a duration sufficient to decrease her responsiveness to recall antigens.

* * * * *

UNITED STATES PATENT AND TRADEMARK OFFICE
CERTIFICATE OF CORRECTION

PATENT NO. : 6,182,665 B1  
APPLICATION NO. : 09/087723  
DATED : February 6, 2001  
INVENTOR(S) : Hill et al.

It is certified that error appears in the above-identified patent and that said Letters Patent is hereby corrected as shown below:

In column 1, lines 11-13, of the issued patent, the paragraph after "Statement of Government Funding" should be corrected to specify the source of funding. The corrected paragraph should read as follows:

-- This invention was made with Government support under Grant Nos. A1038515 and HD023547 awarded by the National Institutes of Health. The U.S. Government therefore has certain rights in the invention. --

Signed and Sealed this

Eighteenth Day of August, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 6,182,665 B1 | Page 1 of 1 |
| APPLICATION NO. | : 09/087723 | |
| DATED | : February 6, 2001 | |
| INVENTOR(S) | : Hill et al. | |

It is certified that error appears in the above-identified patent and that said Letters Patent is hereby corrected as shown below:

In column 1, lines 11-13, of the issued patent, the paragraph after "Statement of Government Funding" should be corrected to specify the source of funding. The corrected paragraph should read as follows:

-- This invention was made with Government support under Grant Nos. AI038515 and HD023547 awarded by the National Institutes of Health. The U.S. Government has certain rights in this invention. --

This certificate supersedes the Certificate of Correction issued August 18, 2009.

Signed and Sealed this

Thirtieth Day of November, 2010

David J. Kappos
*Director of the United States Patent and Trademark Office*